United States Patent [19]
Hall

[11] Patent Number: 6,110,119
[45] Date of Patent: Aug. 29, 2000

[54] ULTRASOUND COLOR FLOW IMAGING UTILIZING A PLURALITY OF ALGORITHMS

[75] Inventor: Anne L. Hall, New Berlin, Wis.

[73] Assignee: General Electric Company, Milwaukee, Wis.

[21] Appl. No.: 09/224,013

[22] Filed: Dec. 31, 1998

[51] Int. Cl.[7] .................................................. A61B 8/06
[52] U.S. Cl. ............................................................ 600/455
[58] Field of Search .................................. 600/440–441, 600/443, 453–456

[56] References Cited

U.S. PATENT DOCUMENTS

| 5,363,851 | 11/1994 | Hall et al. | 600/454 |
| 5,709,210 | 1/1998 | Green et al. | 600/454 |
| 5,868,676 | 2/1999 | McCabe et al. | 600/454 |
| 5,908,391 | 6/1999 | Muzilla et al. | 600/454 |

*Primary Examiner*—Francis J. Jaworski
*Attorney, Agent, or Firm*—McAndrews, Held & Malloy; Christian G. Cabou; Phyllis Y. Price

[57] ABSTRACT

An ultrasonic imaging system for displaying color flow images includes a receiver which demodulates ultrasonic echo signals received by a transducer array and dynamically focuses the baseband echo signals. A color flow processor includes a plurality of logic units which perform different algorithms based on the type of examination being conducted.

4 Claims, 6 Drawing Sheets

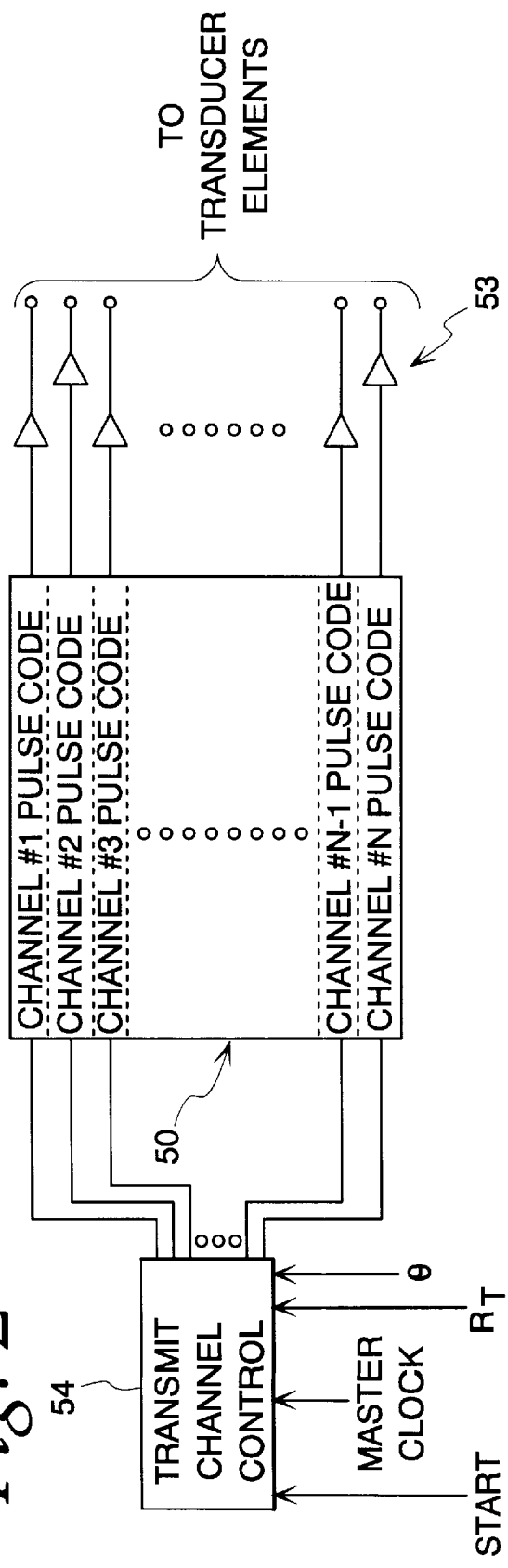
*Fig. 2*
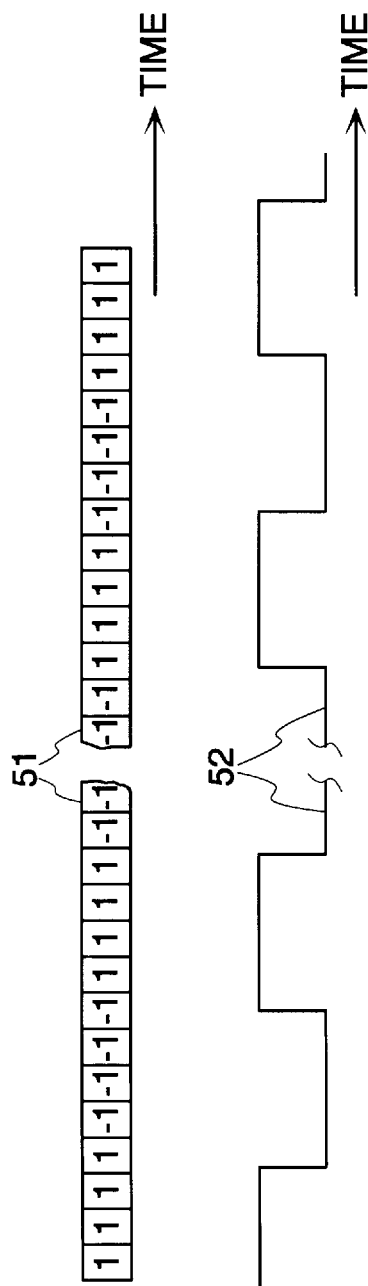
*Fig. 2A*
*Fig. 2B*

ULTRASOUND COLOR FLOW IMAGING UTILIZING A PLURALITY OF ALGORITHMS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to acoustical imaging and, more specifically, relates to the production of colorflow images based on the Doppler shift of ultrasonic signals.

Most mid to high end ultrasound systems include a color flow processor which enables a physician to image blood flow in the body as a tool in the diagnosis of cardiac and vascular dysfunction. Lately this has also been applied to imaging tissue motion. To accomplish this task, the ultrasound system sends and receives a series of firings (packets) along each line of sight, and extracts one or more functional parameters from the return signals using an estimation algorithm. These parameters are then mapped into various colors and displayed as an image overlaying a B mode anatomical image. Traditional parameters extracted are mean blood flow velocity, flow variance, and the strength of the flow signal, or flow power.

Almost all commercial ultrasound systems use an autocorrelation algorithm to extract flow information, since it is a relatively simple, robust algorithm for calculating the mean flow velocity and a crude form of variance can be extracted from its terms. But being a Doppler based estimator, it suffers the same deficiencies as other Doppler based processes, i.e., the reliability of the velocity estimate is inversely linked to the spatial resolution in the image. This deficiency has led investigators to develop a new class of time domain (wideband) estimators having velocity estimate resolution which relies on good spatial resolution. These estimators, however, tend to suffer from signal to noise ratio problems, and are best in high signal noise ratio (SNR) environments.

The autocorrelation algorithm used in most commercial ultrasound systems is useful for estimating material movement characteristics, such as blood flow, in a variety of different portions of a subject under study, such as portions of the human body. However, there are other algorithms which offer advantages for certain portions and certain types of examination. It would be advantageous to have a color flow imaging system which could utilize the best available algorithm for imaging a particular portion of a subject under study and for imaging in connection with a particular type of examination. This invention solves that problem.

BRIEF SUMMARY OF THE INVENTION

The present invention is useful in an ultrasound system comprising a receiver connected to demodulate echo signals received from a subject or patient under study in response to ultrasound waves generated by a vibratory energy transducer. The preferred embodiment includes an improved apparatus and method for providing color display of one or more characteristics of material movement, such as blood flow, in a first portion and a second portion of the subject. As used in this specification and claims, material includes tissue and fluid, such as blood.

According to the preferred embodiment, an operator generates a first input signal indicative of a first type of examination to be conducted and a second input signal indicative of a second type of examination to be conducted. The operator may use a conventional computer keyboard to provide such signals. A first output signal is generated representing at least an estimate of the one or more material movement characteristics based on a first algorithm in response to the first input signal and the echo signals. A second output signal is generated representing at least an estimate of the one or more material movement characteristics based on a second algorithm in response to the second input signal and the echo signals. The generation of the first and second output signals may be accomplished by a microprocessor, microcontroller, microsequencer or other logic unit. The one or more material movement characteristics are displayed in response to the first and second output signals, preferably, by a conventional color flow display unit.

By using the foregoing techniques, the algorithm which is the best suited to determining material movement characteristics for a particular type of examination may be utilized in order to optimize the displayed color flow image. By optimizing the image, the reading of the ultrasound image and the diagnosis based on the reading is enhanced.

BRIEF DESCRIPTION OF THE DRAWINGS

FIG. 2 is a schematic block diagram of a transmitter which forms part of the system of FIG. 1;

FIGS. 2A and 2B are graphical representations of the signal in any of the channels of transmitter 50 of FIG. 2;

DETAILED DESCRIPTION OF THE INVENTION

Figure 1:
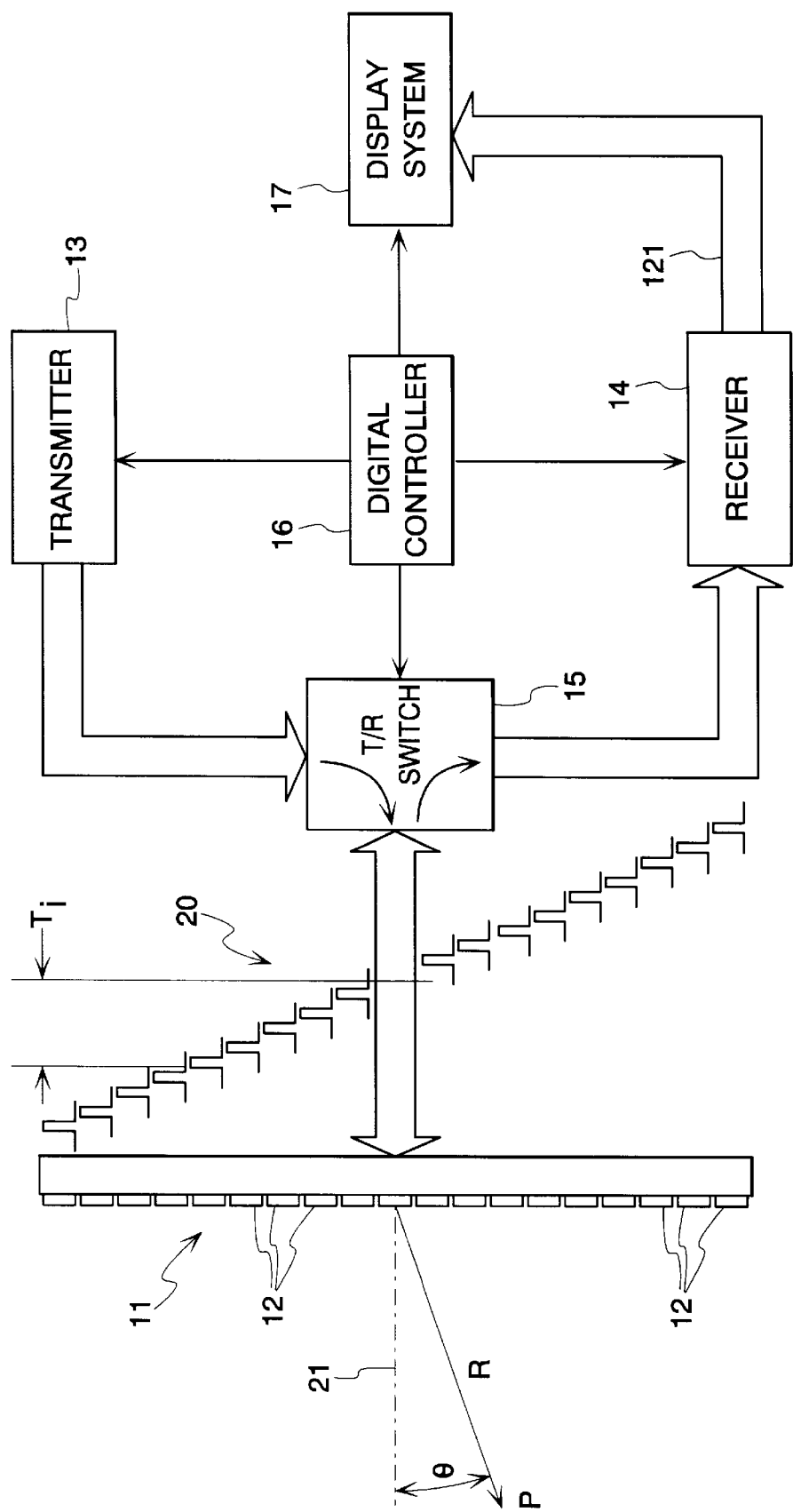
FIG. 1 is a schematic block diagram of an ultrasonic imaging system employing a preferred embodiment of the present invention.

Referring to FIG. 1, a vibratory energy imaging system includes a transducer array 11 comprised of a plurality of separately driven elements 12 which each produce a burst of ultrasonic energy when energized by a pulsed waveform produced by a transmitter 13. The ultrasonic energy reflected back to transducer array 11 from the subject under study is converted to an electrical signal by each transducer element 12 and applied separately to a receiver 14 through a set of transmit/receive (T/R) switches 15. Transmitter 13, receiver 14 and switches 15 are operated under control of a digital controller 16 responsive to commands by a human operator. A complete scan is performed by acquiring a series of echoes in which switches 15 are sent to their transmit position, transmitter 13 is gated on momentarily to energize each transducer element 12, switches 15 are then set to their receive position, and the subsequent echo signals produced by each transducer element 12 are applied to receiver 14. The separate echo signals from each transducer element 12 are combined in receiver 14 to produce a single echo signal which is employed to produce a line in an image on a display system 17.

Transmitter 13 drives transducer array 11 such that the vibrational energy produced, e.g., ultrasonic energy, is directed, or steered, in a beam. A B-scan can therefore be performed by moving this beam through a set of angles from point-to-point rather than physically moving transducer array 11. To accomplish this, transmitter 13 imparts a time delay ($T_i$) to the respective pulsed waveforms 20 that are applied to successive transducer elements 12. If the time delay is zero ($T_i=0$), all the transducer elements 12 are energized simultaneously and the resulting ultrasonic wave is directed along an axis 21 normal to the transducer face. As the time delay ($T_i$) is increased as illustrated in FIG. 1, the ultrasonic wave is directed downward from central axis 21 by an angle θ. The wave is focused at a range $R_T$, thereby forming a beam. The relationship between the time delay $T_i$ applied to each $i^{th}$ signal from one end of the transducer array (i=1) to the other end (i=n) is given by the following relationship:

$$T_i = R_T/c - \sqrt{(R_T/c)^2 + (x/c)^2 - 2xR_T \sin\theta/c^2} \quad (1)$$

where:

x=distance of center of transducer element 12 from center of transducer array;

θtransmit beam angle, c=velocity of sound in the object under study, and $R_T$=range at which transmit beam is focused.

The time delays $T_i$ in equation (1) have the effect of steering the beam in the desired angle θ, and causing it to be focused at a fixed range $R_T$. A sector scan is performed by progressively changing the time delays $T_i$ in successive excitations. The angle θ is thus changed in increments to steer the transmitted beam in a succession of directions. When the direction of the beam is above central axis 21, the timing of pulses 20 is reversed, but the formula of equation (1) still applies.

Referring still to FIG. 1, the echo signals produced by each burst of ultrasonic energy emanate from reflecting objects located at successive positions (R) along the ultrasonic beam. These are sensed separately by each segment 12 of transducer array 11 and a sample of the magnitude of the echo signal at a particular point in time represents the amount of reflection occurring at a specific range (R). Due to the differences in the propagation paths between a reflecting point P and each transducer element 12, however, these echo signals will not occur simultaneously and their amplitudes will not be equal. The function of receiver 14 is to amplify and demodulate these separate echo signals, impart the proper time delay to each and sum them together to provide a single echo signal which accurately indicates the total ultrasonic energy reflected from point P located at R along the ultrasonic beam oriented at the angle θ.

To simultaneously sum the electrical signals produced by the echoes from each transducer element 12, time delays and phase shifts are introduced into each separate transducer element channel of receiver 14. The beam time delays for reception are the same delays ($T_i$) as the transmission delays described above. However, in order to dynamically focus, the time delay and phase shift of each receiver channel is continuously changing during reception of the echo to provide dynamic focusing of the received beam at the range R from which the echo signal emanates. The exact equation for the time delay $T_d$ imposed on the signal received by each transducer element is as follows:

$$T_d = t/2 - \sqrt{(t/2)^2 + (x/c)^2 - (xt/c)\sin(\theta)} \quad (2)$$

where:

t=elapsed time after transmission of sound from center of transducer array (i.e., START), c=velocity of sound in the object under study, θ=beam angle, and x=distance of center of element from center of transducer array.

Under direction of digital controller 16, receiver 14 provides delays during the scan such that steering of receiver 14 tracks with the direction θ of the beam steered by transmitter 13 and it samples the echo signals at a succession of ranges R and provides the proper delays to dynamically focus at points P along the beam. Thus, each emission of an ultrasonic pulse waveform results in the acquisition of a series of data points which represent the amount of reflected sound from a corresponding series of points P located along the ultrasonic beam.

Display system 17 receives the series of data points produced by receiver 14 and converts the data to the form and geometry required to produce the desired image. For example, if an A-scan is desired, the magnitude of the series of data points is merely graphed as a function of time. If a B-scan is desired, each data point in the series is used to control brightness of a pixel in the image, and a scan comprised of a series of measurements at successive steering angles (θ) is performed to provide the data necessary for display.

Referring to FIG. 2 in conjunction with FIG. 1, transmitter 13 includes a set of channel pulse code memories indicated collectively as memories 50. In the preferred embodiment there are 128 separate transducer elements 12, and therefore, there are 128 separate channel pulse code memories 50. Each pulse code memory 50 is typically an n-bit by 512-bit memory which stores a bit pattern 51 that determines the frequency of the ultrasonic pulse 52 to be produced. In the preferred embodiment, this bit pattern is read out of each pulse code memory 50 by a 40 MHz master clock and applied to a driver 53 which amplifies the signal to a power level suitable for driving transducer 11. In the example shown in FIG. 2a, the bit pattern is a sequence of four "1" bits alternated with four "−1" bits to produce a 5 MHz ultrasonic pulse 52; however, other carrier frequencies ($F_0$) may be employed in the preferred embodiment, such as 2.5, 3.75, 6.25, 7.5, 8.75 and 10 MHz. Transducer elements 12 to which these ultrasonic pulses 52 are applied respond by producing ultrasonic energy. If all 512 bits are used, a pulse of bandwidth as narrow as 40 kHz centered on the carrier frequency (i.e. 5 MHz in the example) will be emitted.

As indicated above, to steer the transmitted beam of the ultrasonic energy in the desired direction (θ), pulses 52 for each of the n channels, such as shown in FIG. 2B, must be delayed by the proper amount. These delays are provided by a transmit control 54 which receives four control signals (START, MASTER CLOCK, $R_T$ and θ) from digital controller 16 (FIG. 1). Using the input control signal θ, the fixed transmit focus $R_T$, and the above equation (1), transmit control 54 calculates the delay increment $T_i$ required between successive transmit channels. When the START control signal is received, transmit control 54 gates one of four possible phases of the 40 MHz MASTER CLOCK signal through to the first transmit channel 50. At each successive delay time interval ($T_i$) thereafter, the 40 MHz MASTER CLOCK signal is gated through to the next channel pulse code memory 50 until all n=128 channels are producing their ultrasonic pulses 52. Each transmit channel 50 is reset after its entire bit pattern 51 has been transmitted and transmitter 13 then waits for the next θ and next START control signals from digital controller 16. As indicated above, in the preferred embodiment of the invention a complete B-scan is comprised of 128 ultrasonic pulses steered in Δθ increments which may vary as a function of θ through a 90° sector centered about central axis 21 (FIG. 1) of the transducer 11.

For a detailed description of the transmitter 13, reference is made to commonly assigned U.S. Pat. No. 5,014,712 issued May 14, 1991 and entitled "Coded Excitation For Transmission Dynamic Focusing of Vibratory Energy Beam" incorporated herein by reference.

Figure 3:
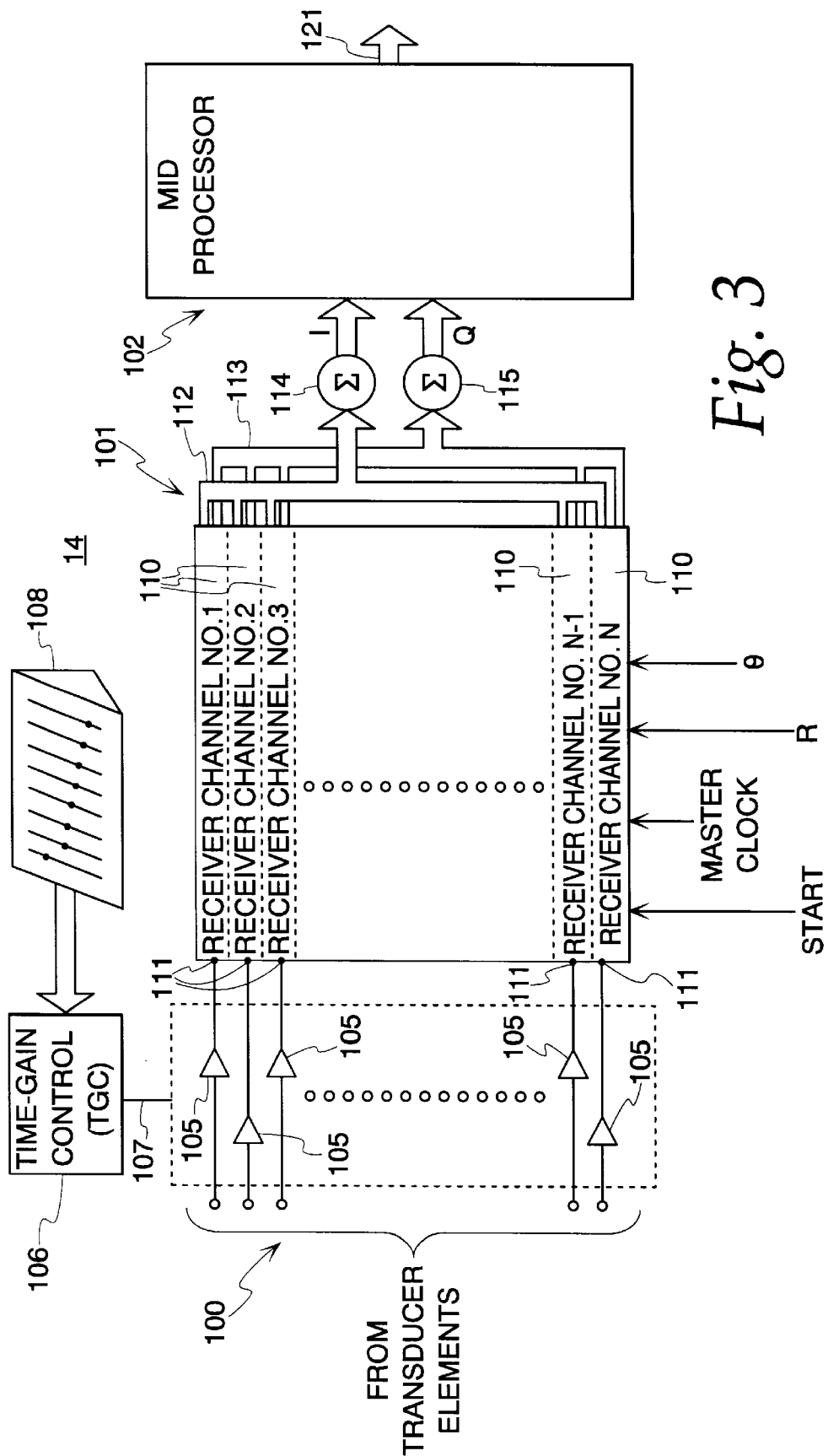
FIG. 3 is a schematic block diagram of a receiver which forms part of the system of FIG. 1.

Referring particularly to FIG. 3, receiver 14 is comprised of these sections: a time-gain control section 100, a receive beam forming section 101, and a mid processor 102. Time-gain control (or TGC) section 100 includes an amplifier 105 for each of the n=128 receiver channels and a time-gain control circuit 106. The input of each amplifier 105 is connected to a respective one of transducer elements 12 to receive and amplify the echo signal which it receives. The amount of amplification provided by amplifiers 105 is controlled through a control line 107 that is driven by TGC circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). The amplification is provided in part by a base gain curve which generally is a linear ramp. The base gain curve is adjusted by the operator who manually sets eight (typically) TGC linear potentiometers 108 to values which provide a relatively uniform brightness over the entire range of the section scan. The time interval over which the echo signal is acquired determines the range from which it emanates, and this time interval is divided into eight segments by TGC circuit 106. The settings of the eight potentiometers are employed to set the gains of amplifiers 105 during each of the eight respective time intervals so that the echo signal is amplified in ever increasing amounts over the echo signal acquisition time interval.

The receive beam forming section 101 of receiver 14 includes 128 separate receiver channels 110. As will be explained in more detail below, each receiver channel 110 receives the analog echo signal from one of amplifiers 105 at an input 111, and it produces a stream of digitized output values on an I bus 112 and a Q bus 113. Each of these I and Q values represents a demodulated sample of the echo signal envelope at a specific range (R). These samples have been delayed such that when they are summed at summing points 114 and 115 with the I and Q samples from each of the other receiver channels 110, they indicate the magnitude and phase of the echo signal reflected from a point P located at range R on the steered beam (θ). In the preferred embodiment, each echo signal is sampled at 150 micrometer increments over the entire range of the scan line (typically 40 to 200 millimeters).

For a more detailed description of receiver 14, reference is made to commonly assigned U.S. Pat. No. 4,983,970, issued Jan. 8, 1991 and entitled "Method And Apparatus for Digital Phase Array Imaging", which is incorporated herein by reference.

Referring still to FIG. 3, mid processor section 102 receives the beam samples from summing points 114 and 115. The I and Q values of each beam sample are 20-bit digital numbers representing the in-phase and quadrature components of the magnitude of the reflected sound from a point (R,θ). Mid processor 102 can perform a variety of calculations on these beam samples, where choice is determined by the type of image to be reconstructed. For example, if a conventional magnitude image is to be produced, a detection logic unit 120 (FIG. 5) is implemented in which a digital magnitude M is calculated from each receive beam sample and produced at output 121 along with the R,θ coordinates of the reflection point, according to $$M = \sqrt{I^2 + Q^2} \tag{3}$$

Detection logic unit 120 may also implement correction methods such as that disclosed in commonly assigned U.S. Pat. No. 4,835,689, issued May 30, 1989 and entitled "Adaptive Coherent Energy Beam Formation Using Phase Conjungation". Such correction methods examine the received beam samples and calculate corrective values that can be used in subsequent measurements by transmitter 13 and receiver 14 to improve beam focusing and steering. Such corrections are necessary, for example, to account for the nonhomogeneity of the media through which the sound from each transducer element travels during a scan.

Figure 5:
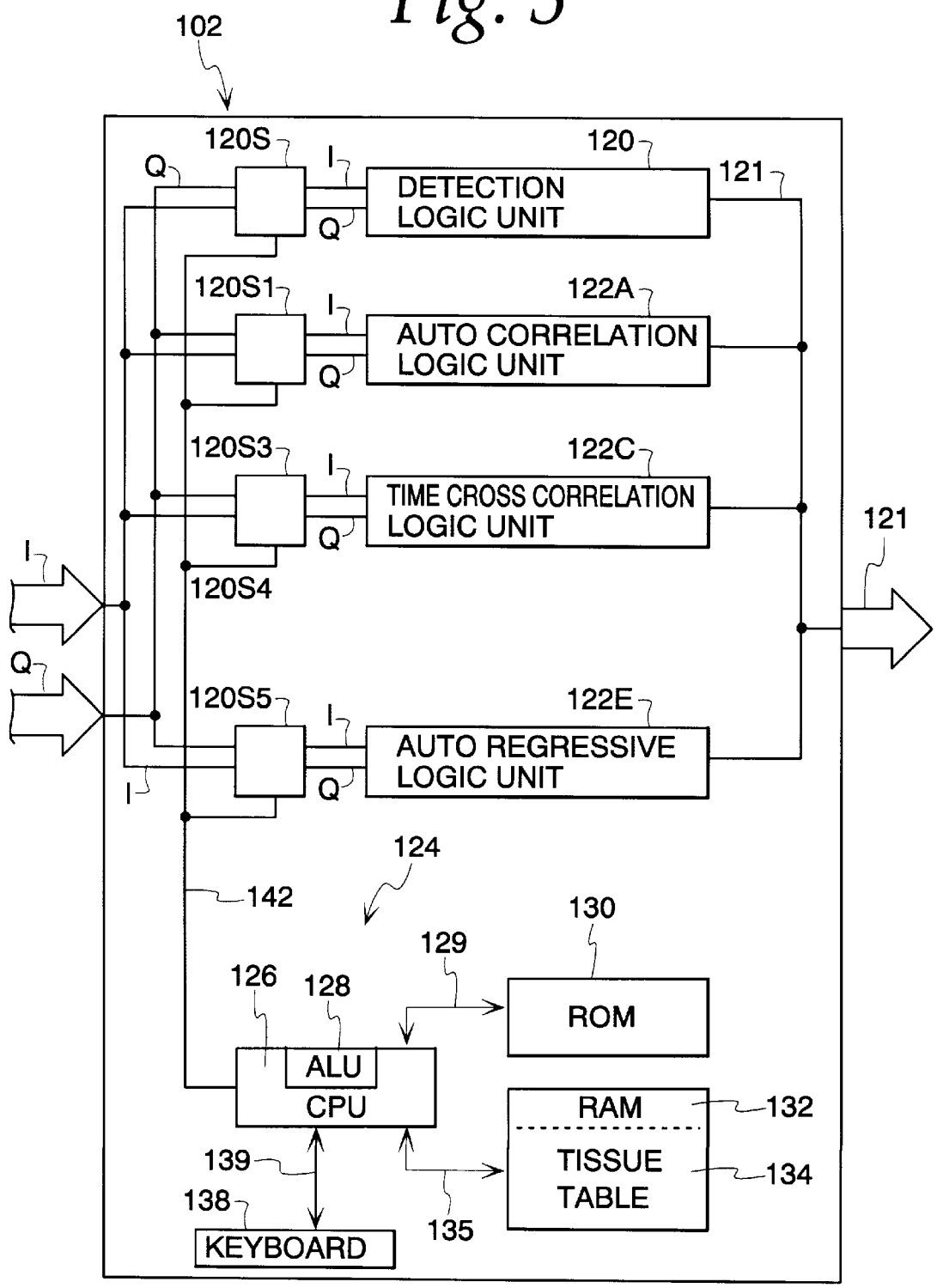
FIG. 5 is one form of the mid-processor 102 illustrated in FIG. 3.

Referring to FIG. 5, mid-processor 102 comprises the detection logic unit 120 which operates as previously described.

Figure 6:
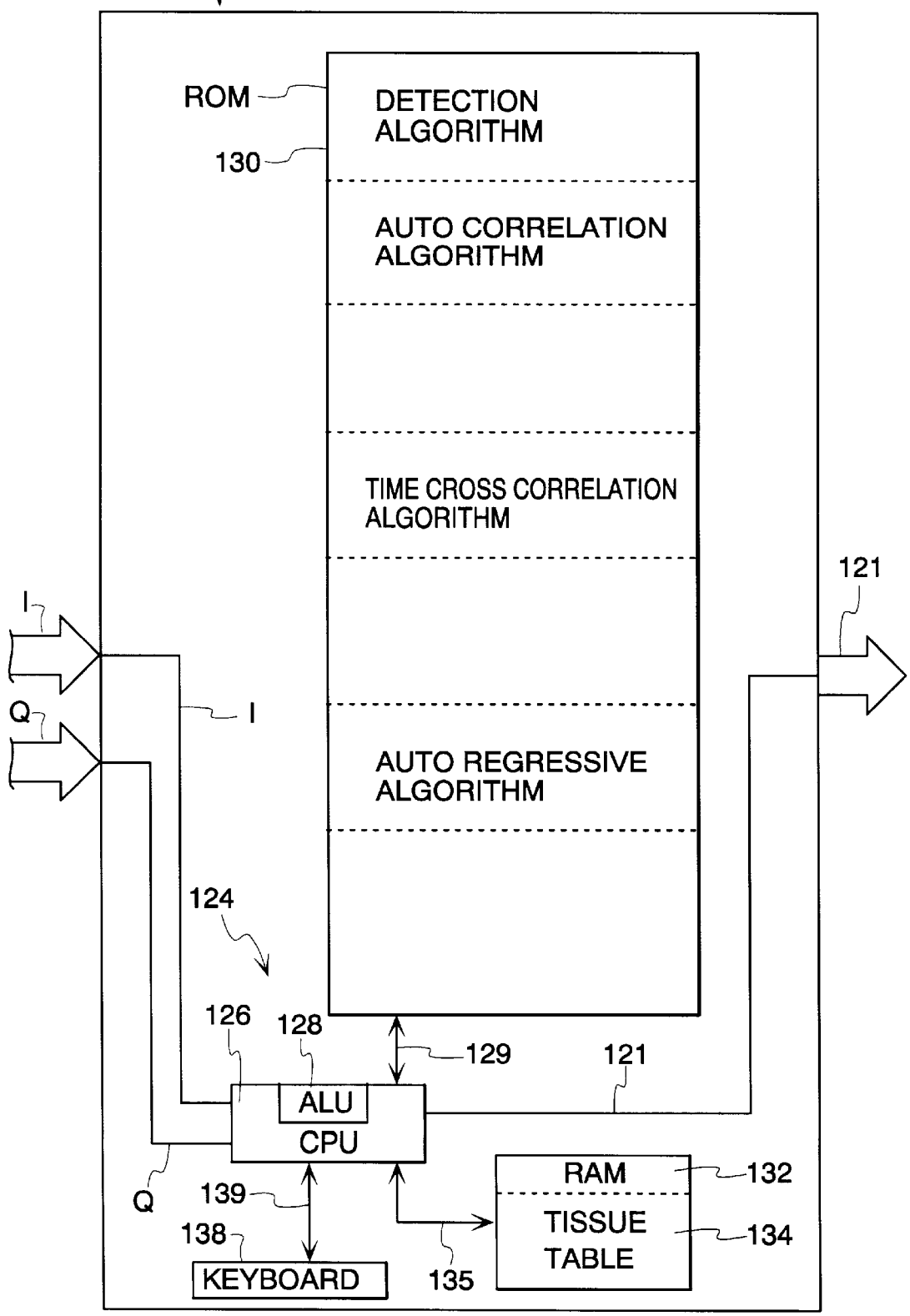
FIG. 6 is another form of the mid-processor 102 shown in FIG. 3.

Processor 102 also includes an autocorrelation logic unit 122 A which may be constructed in the manner shown in FIG. 6 of U.S. Pat. No. 5,349,524 (Daft et al.) assigned to the same assignee as the present application and incorporated by reference.

Processor 102 also includes a time correlation logic unit 122 C which generates an output signal representing an estimate of one or more blood flow characteristics in response to the echo signals on buses I and Q based on the algorithm described in "Time Domain Formulation of Pulse-Doppler Ultrasound and Blood Velocity Estimation By Cross Correlation" by Bonnerous et al. published in *Ultrasonic Imaging*, published by Academic Press, Inc. (1986), pages 73–85. Unit 122 C may be designed by those skilled in the art in accordance with the information provided in the Bonnerous et al. article which is incorporated by reference.

Processor 102 also includes an autoregressive logic unit 122E which generates an output signal representing at least an estimate of one or more blood flow characteristics based on the algorithm described in "Low-Order Complex AR Models for Mean and Maximum Frequency Estimation in the Context of Doppler Color Flow Mapping," by Loupas et al., published in the IEEE Transactions On Ultrasonics, Ferro Electronics and Frequency Control, Vol. 37, No. 6, November 1990 which is incorporated by reference. Unit 122E may be designed in accordance with the information provided in the Loupas et al. article.

Each of the logic units 120 and 122A, 122C and 122E may be hardwired sequential logic circuits, microprocessors, microsequencers, microcontrollers, digital signal processors or the like which are capable of executing the algorithms described in the referenced publications.

Still referring to FIG. 5, processor 102 also includes a digital signal processor, microprocessor, microsequencer, or microcontroller 124 which comprises a central processing unit (CPU) 126 that includes an arithmetic logic unit (ALU) 128. CPU 126 is connected to a read only memory (ROM) 130 through addressing and data busses 129. ROM 130 includes instructions which are executed by CPU 126. The CPU 126 also is connected to a random access memory (RAM) 132 which includes an examination type table 134 and is connected through address and data busses 135. A conventional computer keyboard 138 is connected to CPU 126 through a conventional cable 139. Busses I and Q are connected to logic units 120 and 122A, 122C and 122E through conventional gating switches 120S and 122S1, 122S3 and 122S5, respectively, each connected as shown. Each of the gating switches is programmed to be responsive to an address code which is transmitted from CPU 126 over a conventional bus 142.

Still referring to FIG. 5, in operation, an operator determines the portion of the subject to be imaged and displayed in color and selects the type of the examination on keyboard 138. Keyboard 138 generates a corresponding signal in a register (not shown). CPU 126 periodically scans the keyboard 138 in a well known manner and responds to the examination type identifying signal by addressing a corresponding entry in examination type table 134 which returns a code identifying the logic unit shown in FIG. 5 which is suitable for estimating various material movement characteristics, such as blood flow characteristics. The corresponding logic unit is addressed over bus 142, and the corresponding gating switch is thereby opened to allow signals on busses I and Q to enter the logic unit. As a result, the corresponding logic unit generates an output signal which estimates one or more material movement characteristics, such as blood flow characteristics, and transmits the signal over an output bus 121.

For example, if a word indicating thyroid examination type is entered on keyboard 38, CPU opens gate switch 122S1 to allow signals on busses I and Q to enter autocorrelation logic unit 122A. If, on the other hand, a word indicating carotid examination type is entered on keyboard 138, CPU transmits an address over bus 142 which opens gate switch 122S3 thereby allowing signals on busses I and Q to enter time cross correlation logic unit 122B. As a result of this operation, the operator is able to select the logic unit which provides the most appropriate analysis for the blood flow in the tissue and portion of the subject under consideration.

FIG. 6 illustrates an embodiment of processor 102 in which each of the algorithms identified in connection with FIG. 5 is stored as a series of instructions in read only memory 130 and is executed by CPU 126. As shown in FIG. 6, a detection algorithm, autocorrelation algorithm, time cross correlation algorithm, and autoregression algorithm are each stored in separate sections of read only memory 130 in accordance with the above-referenced articles described in connection with units 120, and 122A, 122C, and 122E, respectively. In operation, the examination type is entered on keyboard 138 in the manner previously described. In response to the word, CPU 126 addresses examination type table 134 and retrieves an identification of the algorithm which is suitable for analysis of the material movement to be imaged. CPU 126 then addresses the appropriate section of read only memory 130, retrieves the instructions for the algorithm sequentially and then executes the instructions. As a result of the execution of the instructions by ALU 128, one or more output signals is generated on output bus 121 which is an estimate of one or more material movement characteristics, such as blood flow characteristics, based on the algorithm represented by the instructions.

Figure 4:
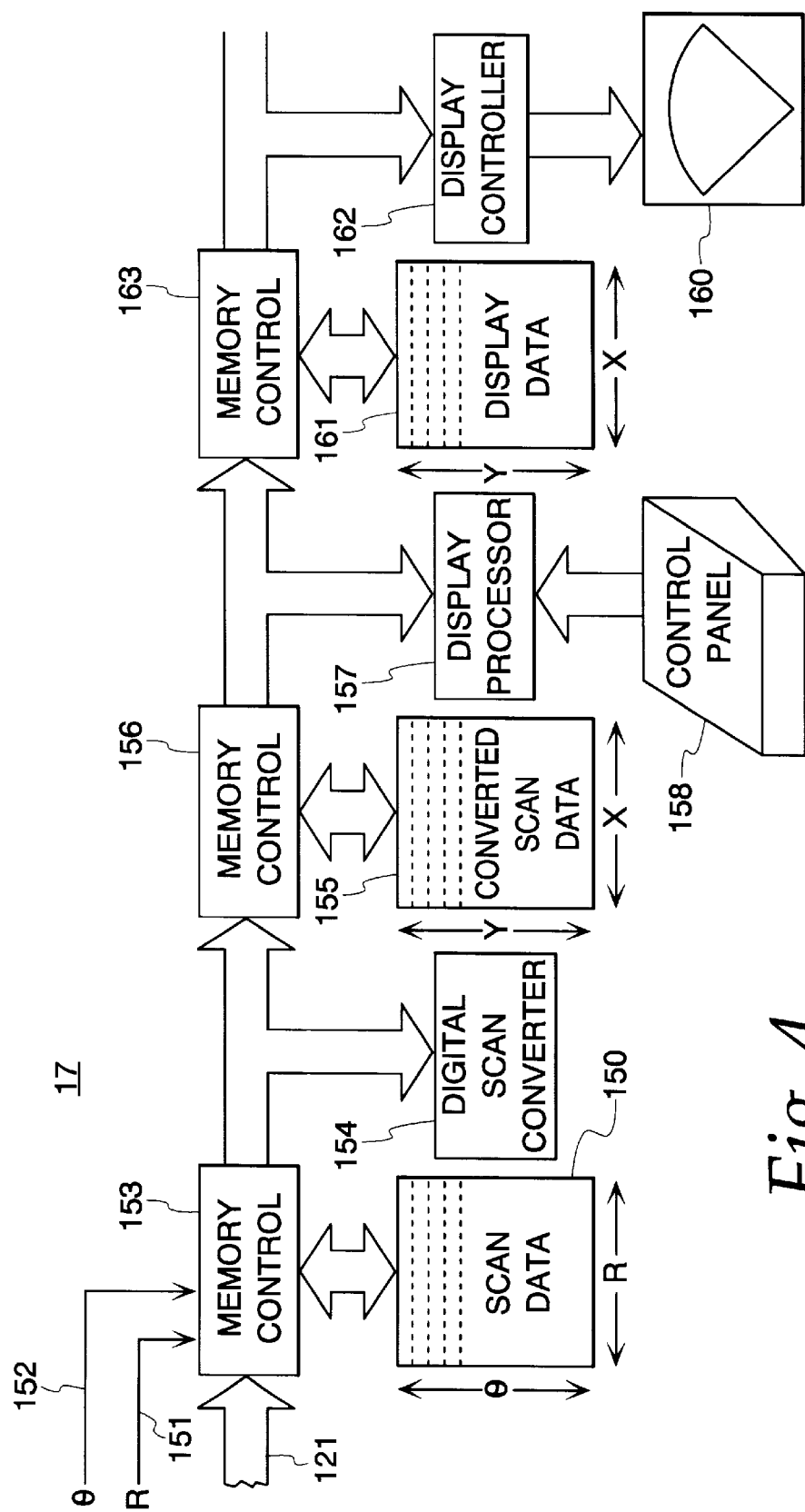
FIG. 4 is a schematic block diagram of the display system which forms part of the system of FIG. 1.

Referring particularly to FIGS. 1 and 4, receiver 14 generates a stream of 8-bit digital numbers at its output 121, which is applied to the input of display system 17. Each output includes an 8-bit tissue magnitude and a 12-bit flow value. These "scan data" are stored in a memory 150 as an array, with the rows of scan data array 150 corresponding with the respective beam angles ($\theta$) that are acquired, and the columns of scan data array 150 corresponding with the respective ranges (R) at which samples are acquired along each beam. The R and $\theta$ control signals 151 and 152 from receiver 14 indicate where each input value is to be stored in array 150, and a memory control circuit 153 writes that value to the proper memory location in array 150. The scan can be continuously repeated and the flow of values from receiver 14 will continuously update scan data array 150.

Referring still to FIG. 4, the scan data in array 150 are read by a digital scan converter 154 and converted to a form producing the desired image. If a conventional B-scan image is being produced, for example, the tissue magnitude and flow values $M(R,\theta)$ stored in the scan data array 150 are converted to values $M(x,y)$ which indicate gray shade (for tissues) and color (for flow) at pixel locations (x,y) in the image. Such a polar coordinate to Cartesian coordinate conversion of the ultrasonic image data is described for example, in an article by Steven C. Leavitt et al. in Hewlett-Packard Journal, October 1983, pp. 30–33, entitled "A Scan Conversion Algorithm for Displaying Ultrasonic Images".

Regardless of the particular conversion made by digital scan converter 154, the resulting image data are written to a memory 155 which stores a two-dimensional array of converted scan data. A memory control 156 provides dual-port access to memory 155 such that digital scan converter 154 can continuously update the values therein with fresh data while a display processor 157 reads the updated data. Display processor 157 is responsive to operator commands received from a control panel 158 to perform conventional image processing functions on the converted scan data in memory 155. For example, the range of brightness levels indicated by the converted scan data in memory 155 may far exceed the brightness range of display device 160. Indeed, the brightness resolution of the converted scan data in memory 155 may far exceed the brightness resolution of the human eye, and manually operable controls are typically provided which enable the operator to select a window of brightness values over which maximum image contrast is to be achieved. The display processor reads the converted scan data from memory 155, provides the desired image enhancement, and writes the enhanced values to a display memory 161.

Display memory 161 is shared with a display controller circuit 162 through a memory control circuit 163, and the values therein are mapped to control brightness and color of the corresponding pixels in display 160. Display controller 162 is a commercially available integrated circuit which is designed to operate the particular type of display 160 used. For example, display 160 may be a CRT (cathode ray tube), in which case display controller 162 is a CRT controller chip which provides the required sync pulses for the horizontal and vertical sweep circuits and maps the display data to the CRT at the appropriate time during the sweep.

It should be apparent to those skilled in the art that display system 17 may take one of many forms depending on the capability and flexibility of a particular ultrasound system. In the preferred embodiment described above, programmed microprocessors are employed to implement the digital scan converter and display processor functions, and the resulting display system is, therefore, very flexible and powerful.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. In an ultrasound system comprising a receiver connected to demodulate echo signals received from a subject under study in response to ultrasound waves generated by a vibratory energy transducer, improved apparatus for providing a color display of one or more characteristics of material movement in a first portion and a second portion of the subject comprising in combination:

an input connected to receive a first input signal indicative of a first type of examination of the subject and a second input signal indicative of a second type of examination of the subject;

one or more logic units responsive to the echo signals and connected to generate a first output signal representing at least an estimate of the one or more material movement characteristics based on a first algorithm comprising a time cross correlation algorithm in response to the first input signal and to generate a second output signal representing at least an estimate of the one or more material movement characteristics based on a second algorithm comprising an autoregressive algorithm in response to the second input signal; and a display unit responsive to the first and second output signals for displaying the one or more material movement characteristics.

2. In an ultrasound system comprising a receiver connected to demodulate echo signals received from a subject under study in response to ultrasound waves generated by a vibratory energy transducer, an improved method of providing a color display of one or more characteristics of material movement of the subject comprising the steps of:

receiving a first input signal indicative of a first type of examination;

receiving a second input signal indicative of a second type of examination;

generating a first output signal representing at least an estimate of the one or more material movement characteristics based on a first algorithm comprising a time cross correlation algorithm in response to the first input signal and the echo signals;

generating a second output signal representing at least an estimate of the one or more material movement characteristics based on a second algorithm comprising an autoregressive algorithm in response to the second input signal and the echo signals; and displaying the one or more material movement characteristics in response to the first output signal and second output signal.

3. In an ultrasound system comprising a receiver connected to demodulate echo signals received from a subject under study in response to ultrasound waves generated by a vibratory energy transducer, improved apparatus for providing a color display of one or more characteristics of material movement in a first portion and a second portion of the subject comprising in combination:

an input connected to receive a first input signal indicative of a first type of examination of the subject and a second input signal indicative of a second type of examination of the subject;

one or more logic units responsive to the echo signals and connected to generate a first output signal representing at least an estimate of the one or more material movement characteristics based on a first algorithm comprising an autoregressive algorithm in response to the first input signal and to generate a second output signal representing at least an estimate of the one or more material movement characteristics based on a second algorithm comprising an autocorrelation algorithm in response to the second input signal; and a display unit responsive to the first and second output signals for displaying the one or more material movement characteristics.

4. In an ultrasound system comprising a receiver connected to demodulate echo signals received from a subject under study in response to ultrasound waves generated by a vibratory energy transducer, an improved method of providing a color display of one or more characteristics of material movement of the subject comprising the steps of:

receiving a first input signal indicative of a first type of examination;

receiving a second input signal indicative of a second type of examination;

generating a first output signal representing at least an estimate of the one or more material movement characteristics based on a first algorithm comprising an autoregressive algorithm in response to the first input signal and the echo signals;

generating a second output signal representing at least an estimate of the one or more material movement characteristics based on a second algorithm comprising an autocorrelation algorithm in response to the second input signal and the echo signals; and displaying the one or more material movement characteristics in response to the first output signal and second output signal.

* * * * *